(12) United States Patent
Boernert et al.

(10) Patent No.: US 8,948,536 B2
(45) Date of Patent: Feb. 3, 2015

(54) DYNAMIC CONTRAST ENHANCED MR IMAGING WITH COMPRESSED SENSING RECONSTRUCTION

(75) Inventors: Peter Boernert, Hamburg (DE); Mariya Doneva, Hamburg (DE)

(73) Assignee: Koninklijke Philips N.V., Eindhoven (NL)

( * ) Notice: Subject to any disclaimer, the term of this patent is extended or adjusted under 35 U.S.C. 154(b) by 105 days.

(21) Appl. No.: 13/805,799

(22) PCT Filed: May 30, 2011

(86) PCT No.: PCT/IB2011/052364
§ 371 (c)(1),
(2), (4) Date: Dec. 20, 2012

(87) PCT Pub. No.: WO2011/161566
PCT Pub. Date: Dec. 29, 2011

(65) Prior Publication Data
US 2013/0089271 A1    Apr. 11, 2013

(30) Foreign Application Priority Data
Jun. 24, 2010    (EP) .................................... 10167157

(51) Int. Cl.
*G06K 9/40* (2006.01)
*G06T 5/00* (2006.01)
(Continued)

(52) U.S. Cl.
CPC ............... *G06T 5/007* (2013.01); *G01N 24/08* (2013.01); *G01R 33/4828* (2013.01);
(Continued)

(58) Field of Classification Search
CPC ............. G06T 5/40; G06T 5/001; G06T 5/50; G06T 5/20; H04N 5/20; H04N 7/30; H04N 7/50; H04N 7/26244; H04N 7/26313; H04N 7/26106
USPC ................. 382/131, 228, 274, 233, 232, 254; 324/306, 307, 309, 313; 600/416
See application file for complete search history.

(56) References Cited

U.S. PATENT DOCUMENTS 6,016,057 A    1/2000  Ma
6,856,134 B1   2/2005  Reeder et al.
(Continued)

FOREIGN PATENT DOCUMENTS

WO    WO 2005/004703    *    1/2005

OTHER PUBLICATIONS

Berglund, J., et al.; Single-image water/fat separation; 2010; ISMRM; #2907.
(Continued)

*Primary Examiner* — Anh Do

(57) ABSTRACT

The present invention relates to a method of performing dynamic contrast enhanced magnetic resonance imaging of an object (10) with signal separation for water and fat, the method comprising acquiring magnetic resonance datasets in the k-space using Dixon acquisition in a chemical shift encoding space and dynamic time resolution in a dynamic time space, wherein the dataset acquisition is performed employing undersampling, wherein the method further comprises: applying a compressed sensing reconstruction technique in the k-space, the chemical shift encoding space and the dynamic time space, said compressed sensing reconstruction resulting in reconstructed datasets, —performing Dixon reconstruction on the reconstructed datasets and dynamic contrast analysis on the Dixon reconstructed datasets.

20 Claims, 3 Drawing Sheets

(51) Int. Cl.
| | |
|---|---|
| *G01N 24/08* | (2006.01) |
| *G01R 33/48* | (2006.01) |
| *G01R 33/561* | (2006.01) |
| *G01R 33/563* | (2006.01) |
| *G01R 33/56* | (2006.01) |

(52) U.S. Cl.
CPC ..... *G01R 33/5611* (2013.01); *G01R 33/56308* (2013.01); *G01R 33/5635* (2013.01); *G01R 33/5601* (2013.01); *G01R 33/5607* (2013.01); *G01R 33/5615* (2013.01)
USPC ............ 382/274; 382/232; 382/233; 382/254

(56) References Cited

U.S. PATENT DOCUMENTS

| | | | | |
|---|---|---|---|---|
| 7,298,144 | B2 | 11/2007 | Reeder et al. | |
| 7,486,073 | B2* | 2/2009 | Yu et al. ........................ | 324/307 |
| 7,486,074 | B2* | 2/2009 | McKenzie et al. ............ | 324/309 |
| 7,592,810 | B2* | 9/2009 | Reeder et al. ................. | 324/309 |
| 7,741,842 | B2* | 6/2010 | McKenzie et al. ............ | 324/307 |
| 8,064,674 | B2* | 11/2011 | Fenchel et al. ................ | 382/131 |

OTHER PUBLICATIONS

Bilgin, A., et al.; Three-Dimensional Compressed Sensing for Dynamic MRI; 2008; Proc. Intl. Soc. Mag. Reson. Med; 16:337.

Desmond, K. L, et al.; Comparison of Biphasic and Reordered Fat Suppression for Dynamic Breast MRI; 2007; J. MRI; 25:1293-1298.

Doneva, M., et al.; CS-Dixon: Compressed Sensing for Water-Fat Dixon Reconstruction; 2010; ISMRM: 2919.

Gamper, U., et al.; Compressed Sensing in Dynamic MRI; 2008; MRM; 59:365-373.

Glover, G. H., et al.; Three-Point Dixon Technique for True Water/Fat Decomposition with Bo Inhomogeneity Correction; 1991; MRM; 18:371-383.

Ji, J., et al.; Dynamic MRI with Compressed Sensing Imaging Using Temporal Correlations; 2008; Biomedical Imaging: From Nano to Macro; pp. 1613-1616.

Koken, P., et al.; Fast Single Breath-hold 3D Abdominal Imaging with Water-Fat Separation; 2007; Proc. Intl. Soc. Mag. Reson. Med; 15:1623.

Lustig, M., et al.; Sparse MRI: The Application of Compressed Sensing for Rapid MR Imaging; 2007; MRM; 58:1182-1195.

Ma, J.; Dixon Techniques for Water and Fat Imaging; 2008; J. MRM; 28:543-558.

Narayan, S., et al.; Case-PDM Optimized Compressed Sensing Sampling for Fat-Water Separation; 2010; Internet citation; pp. 3157.

Narayan, S., et al.; Comparison of Compressed Sensing and Keyhole Methods for Fat-Water Separation; 2010; Internet citation; pp. 3158.

Otazo, R., et al.; Highly-accelerated first-pass cardiac perfusion MRI using compressed sensing and parallel imaging; 2010; J. of Cardiovascular Magnetic Resonance; 12(suppl 1)071.

Reeder, S. B., et al.; Iterative Decomposition of Water and Fat with Echo Asymmetry and Least-Squares Estimation (IDEAL): Application with Fast Spin-Echo Imaging; 2005; MRM; 54(3)636-644.

Reeder, S. B., et al.; Multicoil Dixon Chemical Species Separation with an Iterative Least-Squares Estimation Method; 2004; MRM; 51(1)35-45.

Sharma, S. D., et al.; Acceleration of IDEAL Water-Fat Imaging using Compressed Sensing; 2010; Internet citation; pp. 4884.

Xiang; Q-S.; Two-Point Water-Fat Imaging with Partially-Opposed-Phase (POP) Acquisition: An Asymmetric Dixon Method; 2006; MRM; 56(3)572-584.

\* cited by examiner

DYNAMIC CONTRAST ENHANCED MR IMAGING WITH COMPRESSED SENSING RECONSTRUCTION

FIELD OF THE INVENTION

The invention relates to a method of performing dynamic contrast enhanced magnetic resonance imaging with compressed sensing reconstruction, as well as a computer product and a magnetic imaging apparatus for performing dynamic contrast enhanced magnetic resonance imaging of an object.

BACKGROUND OF THE INVENTION

Image-forming MR methods which utilize the interaction between magnetic field and nuclear spins in order to form two-dimensional or three-dimensional images are widely used nowadays, notably in the field of medical diagnostics, because for the imaging of soft tissue they are superior to other imaging methods in many respects and do not require ionizing radiation and they are usually not invasive.

According to the MR method in general, the body of a patient or in general an object to be examined is arranged in a strong, uniform magnetic field B0 whose direction at the same time defines an axis, normally the z-axis, of the coordinate system on which the measurement is based. The magnetic field produces different energy levels for the individual nuclear spins in dependence on the applied magnetic field strength which spins can be excited (spin resonance) by application of an alternating electromagnetic field (RF field) of defined frequency, the so called Larmor frequency or MR frequency. From a macroscopic point of view the distribution of the individual nuclear spins produces an overall magnetization which can be deflected out of the state of equilibrium by application of an electromagnetic pulse of appropriate frequency (RF pulse) while the magnetic field extends perpendicularly to the z-axis, so that the magnetization performs a processional motion about the z-axis.

Any variation of the magnetization can be detected by means of receiving RF antennas, which are arranged and oriented within an examination volume of the MR device in such a manner that the variation of the magnetization is measured in the direction perpendicularly to the z-axis.

In order to realize spatial resolution in the body, linear magnetic field gradients extending along the three main axes are superposed on the uniform magnetic field, leading to a linear spatial dependency of the spin resonance frequency. The signal picked up in the receiving antennas then contains components of different frequencies which can be associated with different locations in the body. The signal data obtained via the receiving antennas corresponds to the spatial frequency domain and is called k-space data. The k-space data usually includes multiple lines acquired with different phase encoding. Each line is digitized by collection a number of samples. A sample of k-space data is converted to an MR image, e.g. by means of Fourier transformation.

Dynamic contrast enhanced (DCE) MRI is one of the important diagnostic cornerstones in MRI based breast cancer diagnosis. Time-resolved dynamic imaging is performed during and after the administration (iv) of contrast media (Gd) to monitor signal changes due to contrast media inflow, outflow and perfusion. In this way structural changes in vascular system (including the capillary bed) and the interstitial spaces can be visualized, helping to identify potential tumor. Partial volume effects caused by fat tissue might obscure the contrast enhancement. Therefore, currently spectral fat pre-saturation approaches are used to suppress the fat signal to improve the detectability (compare Desmond K L, et al. JMRI 2007; 25:1293).

B1-/B0-inhomogeneities hamper the quality of overall fat suppression in clinical applications. A too frequently applied chemical shift selective pre-saturation RF pulse could also contribute to SAR (specific absorption rate) limitations, especially in high-field application. Chemical shift encoding approaches, like two- and three-point-Dixon approaches as disclosed for example in Glover G H, et al. MRM 1991; 18:371, Reeder S B, et al. MRM 2004; 51:35, Reeder S B, et al. MRM 2005; 54:636-644 and Xiang Q S. MRM 2006; 56:572-584 allow separating water and fat signals in a more robust way. However, all these Dixon approaches require more data prolonging total scanning time and thus reducing temporal resolution, which is not desirable.

Multi-echo techniques (Koken et al. ISMRM Berlin 2007, 1623), measuring a number of gradient echoes after each RF excitation, could be used for Dixon encoding, but their sampling efficiency is not sufficient to compensate for the extra time needed.

SUMMARY OF THE INVENTION

From the forgoing it is readily appreciated that there is a need for an improved MR imaging method. It is consequently an object of the invention to enable dynamic contrast enhanced magnetic resonance imaging in a fast manner. Further, from the forgoing it is readily appreciated that there is a need for an improved MR imaging system and an improved computer program product adapted to carry out the method according to the invention.

In accordance with the present invention a method of performing dynamic contrast enhanced magnetic resonance imaging of an object with signal separation for water and fat is presented, the method comprising acquiring magnetic resonance datasets in the k-space using Dixon acquisition in a chemical shift encoding space and dynamic time resolution in a dynamic time space, wherein the dataset acquisition is performed employing undersampling, wherein the method further comprises applying a compressed sensing (CS) reconstruction technique in the k-space, the chemical shift encoding space and the dynamic time space, wherein said compressed sensing reconstruction results in reconstructed datasets. Further, Dixon reconstruction is performed on the reconstructed datasets and dynamic contrast analysis is finally performed on the Dixon reconstructed datasets.

In other words it is disclosed to accelerate chemical shift encoded water/fat resolved DCE using appropriate data subsampling and corresponding signal reconstruction. It is further disclosed to accelerate DCE measuring using the concepts of compressed sensing.

Embodiments of the invention have the advantage that the quality of DCE MR data is improved allowing for higher spatial or temporal resolution while keeping the data acquisition time and data processing time low. This permits an improved diagnostic quality of for example DCE-based tumor detection.

Consequently, the invention can for example be used to facilitate accelerated water/fat resolved DCE breast cancer diagnosis.

In accordance with an embodiment of the invention, the datasets are acquired in the k-space, chemical shift encoding space and the dynamic time space employing undersampling. This permits to reducing the scanning time, but still guarantees high image quality due to the CS data reconstruction.

In accordance with a further embodiment of the invention, the compressed sensing reconstruction and Dixon reconstruction are performed together in a combined optimization process. In other words, instead of performing first a compressed sensing reconstruction and second a separate Dixon reconstruction step, these two steps are performed in an integrated manner together.

In accordance with a further embodiment of the invention, the method further comprises acquiring an a priori water-fat image on the object, wherein the compressed sensing reconstruction comprises determining an MR signal model of an expected water-fat image and iteratively linearize the signal model, said iteration being initialized with the a priori water-fat image.

This permits in a fast and reliable manner to perform the compressed sensing reconstruction.

In accordance with a further embodiment of the invention, the a priori water-fat image comprises a water signal, a fat signal and a field map, wherein the compressed sensing reconstruction is performed assuming constraints regarding a temporal behavior of the water signal and/or fat signal and/or the field map in the dynamic time space. Such a priori assumptions (constraints) ensure that the reconstruction process is mathematically further stabilized.

In accordance with a further embodiment of the invention, the a priori water-fat image is acquired with full sampling in the k-space and the chemical shift encoding space. By having a good initial 'estimation' of the field map for a single time frame, the integrated problem of compressed sensing reconstruction and Dixon reconstruction becomes almost linear which makes computation easier and more efficient.

In accordance with a further embodiment of the invention, the k-space center is fully sampled.

In accordance with a further embodiment of the invention, the undersampling is performed randomly or quasi-randomly. This permits to smear artifacts in the reconstructed images in an incoherent manner, which thus improves the MR image quality.

In accordance with a further embodiment of the invention, the magnetic resonance datasets are acquired employing parallel imaging. This further speeds up the data acquisition process.

In accordance with a further embodiment of the invention, the Dixon acquisition is a multi echo Dixon acquisition, preferably a two-point echo Dixon acquisition. Alternatively, the Dixon acquisition may be a single-point Dixon acquisition which is known for example from J. Berglund, H. Ahlström, L. Johansson, and J. Kullberg. Single-image water/fat separation. ISMRM 2010, #2907.

In another aspect, the invention relates to a computer program product comprising computer executable instructions to perform any of the method steps described above.

In another aspect, the invention relates to a magnetic resonance imaging apparatus for performing dynamic contrast enhanced magnetic resonance imaging of an object with signal separation for water and fat, the apparatus comprising:

a magnetic resonance imaging scanner for acquiring magnetic resonance image data, a controller adapted for controlling a scanner operation of acquiring magnetic resonance datasets in the k-space using multi-echo Dixon acquisition in a chemical shift encoding space and dynamic time resolution in a dynamic time space, wherein the controller is further adapted to perform the dataset acquisition employing undersampling, a data reconstruction system adapted for applying a compressed sensing reconstruction technique in the k-space, the chemical shift encoding space and the dynamic time space, said compressed sensing reconstruction resulting in reconstructed datasets, wherein the data reconstruction system is further adapted for performing Dixon reconstruction on the reconstructed datasets and dynamic contrast analysis on the Dixon reconstructed datasets.

Such a system can provide information from water/fat resolved DCE. Besides the better DCE information obtained from the water-only data, the separated fat data can bear interesting tissue structural information. The DCE fat data could further contribute to the diagnoses, and the main field inhomogeneity map, which is influenced by local tissue susceptibility changes, could potentially be helpful supporting the diagnosis.

BRIEF DESCRIPTION OF THE DRAWINGS

In the following, preferred embodiments of the invention are described in greater detail by way of example only. Thus, the following drawings are designed for the purpose of illustration only and not as a definition of the limits of the invention. In the drawings.

DETAILED DESCRIPTION OF THE EMBODIMENTS

Figure 1:
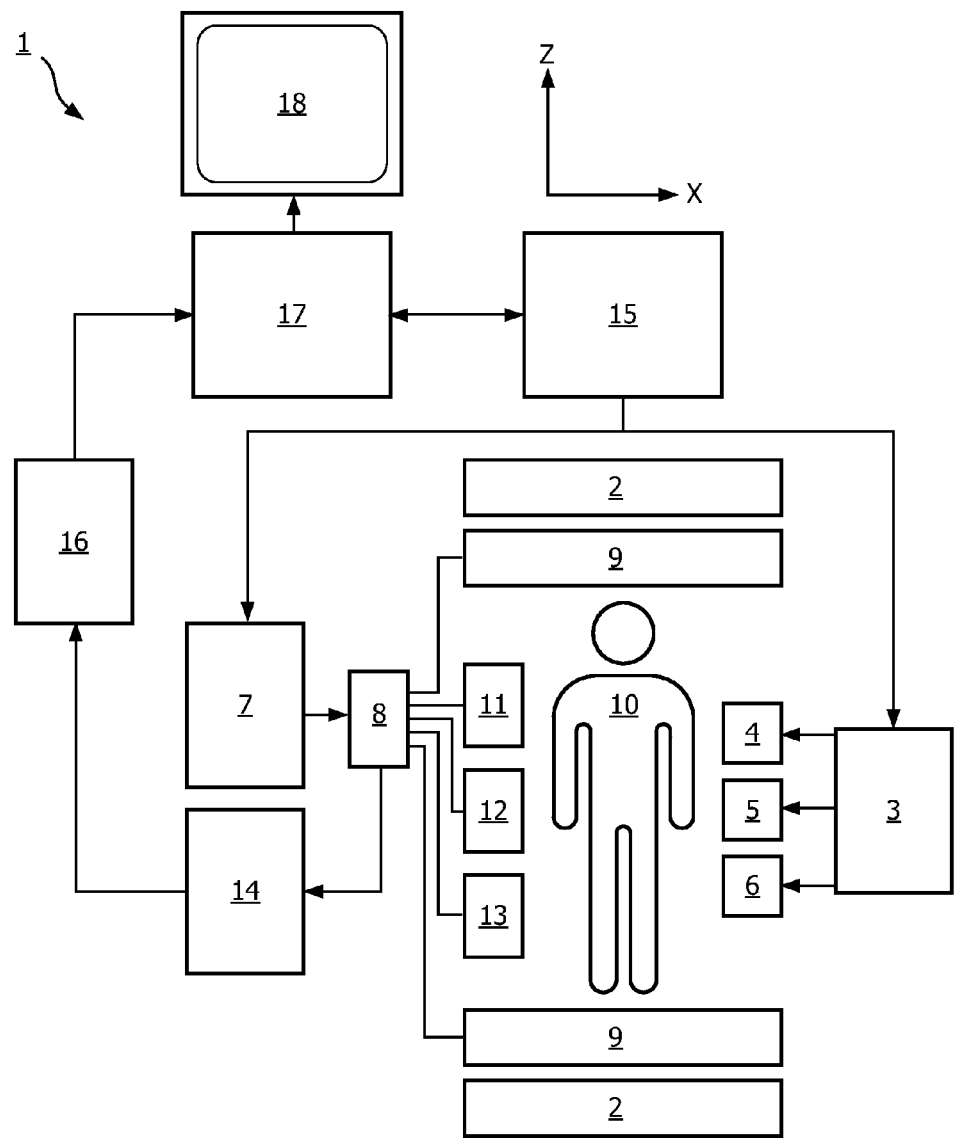
FIG. 1 shows an MR device for implementation of the method according to the invention.

With reference to FIG. 1, an MR imaging system 1 is shown. The system comprises superconducting or resistive main magnet coils 2 such that a substantially uniform, temporarily constant main magnetic field B0 is created along a z-axis through an examination volume.

A magnetic resonance generation manipulation system applies a series of RF pulses and switched magnetic field gradients to invert or excite nuclear magnetic spins, induce magnetic resonance, refocus magnetic resonance, manipulate magnetic resonance, spatially or otherwise encode the magnetic resonance, saturate spins and the like to perform MR imaging.

More specifically, a gradient pulse amplifier 3 applies current pulses to selected ones of whole body gradient coils 4, 5 and 6 along x, y and z-axes of the examination volume. An RF transmitter 7 transmits RF pulses or pulse packets, via a send/receive switch 8 to an RF antenna 9 to transmit RF pulses into the examination volume. A typical MR imaging sequence is composed of a packet of RF pulse sequences of short duration which taken together with each other and any applied magnetic field gradients achieve a selected manipulation of nuclear magnetic resonance. The RF pulses are used to saturate, excite resonance, invert magnetization, refocus resonance, or manipulate resonance and select a portion of a body 10 positioned in the examination volume. The MR signals may also be picked up by the RF antenna 9.

For generation of MR images of limited regions of the body or in general object 10, for example by means of parallel imaging, a set of local array RF coils 11, 12 and 13 are placed contiguous to the region selected for imaging. The array coils 11, 12 and 13 can be used to receive MR signals induced by RF transmissions effected via the RF antenna. However, it is also possible to use the array coils 11, 12 and 13 to transmit RF signals to the examination volume.

The resultant MR signals are picked up by the RF antenna 9 and/or by the array of RF coils 11, 12 and 13 and are demodulated by a receiver 14 preferably including a preamplifier (not shown). The receiver 14 is connected to the RF coils 9, 11, 12 and 13 via a send/receive switch 8.

A host computer 15 controls the gradient pulse amplifier 3 and the transmitter 7 to generate any of a plurality of imaging sequences, such as echo planar imaging (EPI), echo volume imaging, gradient and spin echo imaging, fast spin echo imaging and the like.

For the selected sequence, the receiver 14 receives a single or a plurality of MR data lines in a rapid succession following each RF excitation pulse. A data acquisition system 16 performs analogue to digital conversion of the received signals and converts each MR data line to a digital format suitable for further processing. In modern MR devices the data acquisition system 16 is a separate computer which is specialized in acquisition of raw image data.

Ultimately, the digital raw image data is reconstructed into an image representation by a reconstruction processor 17 which applies a Fourier transform or other appropriate reconstruction algorithms. The MR image may represent a planar slice through the patient, an array of parallel planar slices, a three-dimensional volume or the like. The image is then stored in an image memory where it may be accessed for converting slices or other portions of the image representation into appropriate formats for visualization, for example via a video monitor 18 which provides a man readable display of the resultant MR image.

The host computer 15 may be adapted for controlling a scanner operation of acquiring magnetic resonance datasets in the k-space using multi-echo Dixon acquisition in a chemical shift encoding space and dynamic time resolution in a dynamic time space, wherein
the controller is further adapted to perform the dataset acquisition employing undersampling.

The reconstruction processor 17 is adapted for applying a compressed sensing reconstruction technique in the k-space, the chemical shift encoding space and the dynamic time space, said compressed sensing reconstruction resulting in reconstructed datasets, wherein the data reconstruction system is further adapted for performing Dixon reconstruction on the reconstructed datasets and dynamic contrast analysis on the Dixon reconstructed datasets.

In detail, to facilitate a 3D time resolved water-fat DCE imaging 3D data are acquired for 3 echo times for several dynamics, i.e. in the dynamic time space. As schematically shown the acquisition of the different echoes runs in the inner loop.

| TE1 TE2 TE3 | TE1 TE2 TE3 ... | TE1 TE2 TE3 |
|---|---|---|
| Dynamic 1 | Dynamic 2 | Dynamic N |

As mentioned above, the acquired data are preferable randomly or quasi-randomly undersampled (e.g. by Poisson disk sampling) in the multi-dimensional k-TE-t space with fully sampled k-space center to account for the higher signal energy around the k-space center.

In the most basic implementation each image $x_i$ (for a single TE and single dynamic) is independently reconstructed using compressed sensing reconstruction, the reconstructed images are used as an input in a water-fat separation reconstruction and finally DCE evaluation is performed. The CS reconstruction required solving the following minimization problem $$\min \cdot \|\Psi x_i\|_1 \text{ s.t.} \|F_u x_i - y_i\|_2^2 < \varepsilon \quad (1)$$

$$x = \begin{bmatrix} w \\ f \\ \Delta B_0 \end{bmatrix}$$

Here, x is a vector containing the water image, fat image and the field inhomogeneity (field map). $y_i$ is the corresponding k-space data vector $F_u$ is the undersampled Fourier operator $\Psi$ is a sparsifying transform, e.g. wavelets and $\varepsilon$ is a estimated noise level.

However, this basic implementation permits only a CS reconstruction in k space with separate Dixon reconstruction. Coherences in the k-space (k), the chemical shift encoding space (TE) and the dynamic time space (t) are not considered yet.

An improvement over (1) can be achieved by using the initially computed water, fat and field map from (1) to initialize a simultaneous water-fat CS reconstruction as described in Doneva M, et al. ISMRM Stockholm 2010, 2919.

An integrated water/fat separation CS reconstruction may thus be performed for each dynamic by solving the problem:

$$\min \cdot \|g(w,f,\phi)-y\|_2^2 + \lambda_1(\|\Psi w\|_1 + \|\Psi f\|_1) + \lambda_2\|\Phi\phi\|_2^2 \quad (2)$$

Where w, f, and φ are the water, fat images and field map, respectively. $\Psi$ is again the sparsifying transform (wavelet, finite differences) and $\Phi$ is a smoothness operator (second order finite differences) applied on the field map. The measurement operator g is a nonlinear function of the field map φ, the water and the fat signal forming basically the MR signal model for a water-fat image.

One option to solve the problem (2) is to iteratively linearize g around the current estimate of w, f, φ and solve a linear problem for each iteration. The field map estimate obtained in the above approach (1) can be used for initialization and is usually very close to the solution therefore very few outer iterations (linearization steps) are needed.

However, the implementation (2) permits only a consideration of coherences in the k-space (k) and the chemical shift encoding space (TE). The dynamic time space (t) is still not considered yet.

Thus, to integrate the temporal correlations in the reconstruction (over different dynamics) one can solve the k-t CS problem for each TE, instead of independent reconstruction for each images as described in (1), for instance by solving the problem $$\min \cdot \|\Psi(x_i-x_c)\|_1 s \cdot t \cdot \|F_u x_i - y_i\|_2^2 < \varepsilon \quad (3)$$

Where $x_c$ is a composite image for a given TE and all dynamics and using the reconstructed images to initialize the integrated problem $$\min \cdot \|g(w,f,\phi)-y\|_2^2 + \lambda_1(\|\Psi(w-w_c)\|_1 + \|\Psi(f-f_c)\|_1) + \lambda_2\|\Phi\phi\|_2^2 \quad (4)$$

Where $w_c$ and $f_c$ are the composite water and fat images.

This finally considers coherences in k, TE and t space thus significantly improving the temporal resolution of water/fat resolved DCE, which might also be traded into spatial resolution. In water/fat resolved DCE some data/information redundancy is present because the water/fat tissue composition will remain unchanged during for example contrast media (for example comprising Gd) administration. Thus the basic water/fat composition can be measured in a non-time critical phase of the scan, means prior to contrast media administration and can act as a-priory information, useful to facilitate more drastic sub-sampling.

A contrast agent to be administered is expected to cause changes in the signal over time predominantly in the water and not in the fat images; also the field map is not expected to change. Therefore, it is preferred to define respective constraints for the reconstruction process. Thus, given a good initial estimation of the field map for a single time frame, the problem becomes almost linear for all dynamics. This makes computation easier and more efficient.

Another option to obtain a good estimate of the field map is to perform a fully sampled prescan by means of a three-point measurement before contrast agent administration. The resulting field map is used as initialization. The fat and water images can be used instead of the composite images $w_c$ and $f_c$. Subtracting the initially obtained water and fat images from each time frame during contrast agent administration could be a useful sparsifying transform. The field inhomogeneity map ($\Delta B_0$) could be used for initialization of the Gauss-Newton algorithm.

The reconstruction can be further extended to use phased arrays by replacing/extending the Fourier transform with the encoding function associated with the phased array, including the coil sensitivities.

Further acceleration can be achieved if a two-point or even single point Dixon measurement is used for water-fat encoding. This helps to further reduce the measurement time.

Figure 2A:
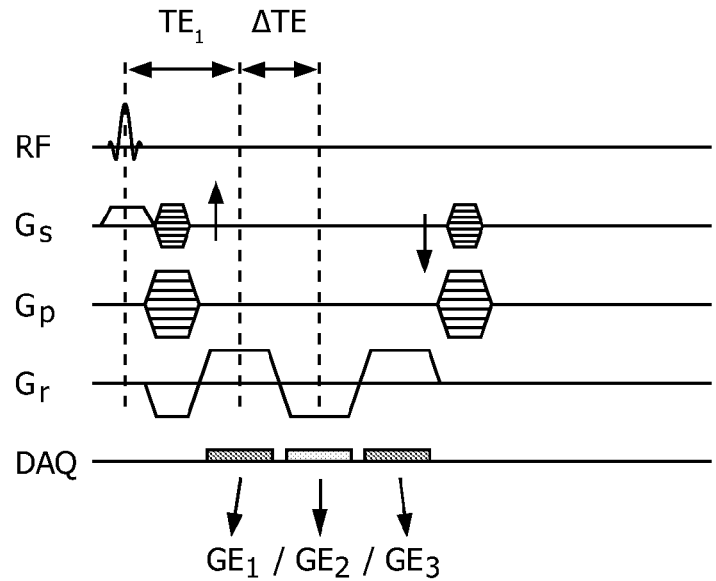
FIG. 2a and FIG. 2b show examples for two different efficient three-point Dixon data acquisition schemes.
Figure 2B:
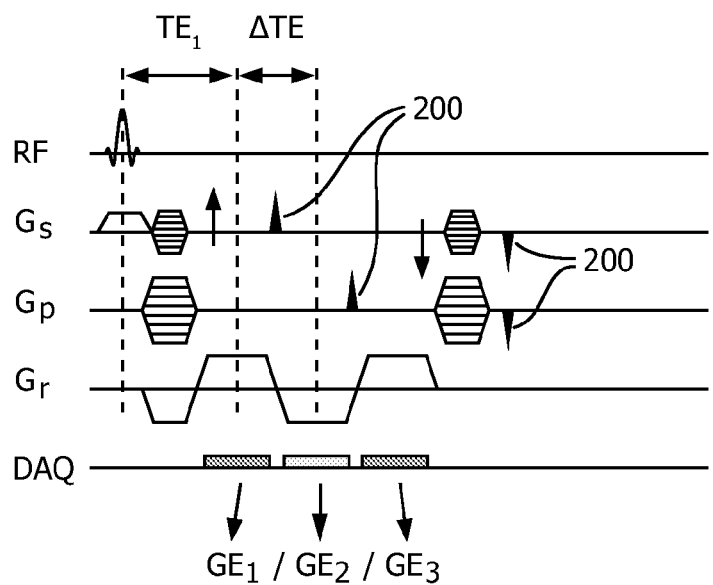

FIG. 2a and FIG. 2b show examples for two different efficient 3-point Dixon data acquisition schemes. Three-point Dixon (chemical shift encoding) is applied in a multi-echo mode, wherein three gradient echoes (GE1, GE2, GE3) are acquired (DAQ —data acquisition) after one RF excitation. (a) For the same phase encoding step k, chemical shift encoded data are sampled. (b) Sub-sampling is performed in the k-direction. In a random fashion corresponding phase encoding blips (200) are applied to measure for different encoding times different k-space samples.

Thus, the sequence performs under-sampling in a way that less profiles are acquired in the chemical shift dimension and that the multi-gradient echo mode is slightly modified allowing for phase encoding blip gradients to address different phase encoding steps in this echo train for high scan efficiency. Finally, data are reconstructed using a DCE water/fat resolved CS reconstruction as described above. In this water/fat resolved DCE data are available for further analysis, which were acquired without a time penalty with respect to conventional approaches.

Figure 3A:
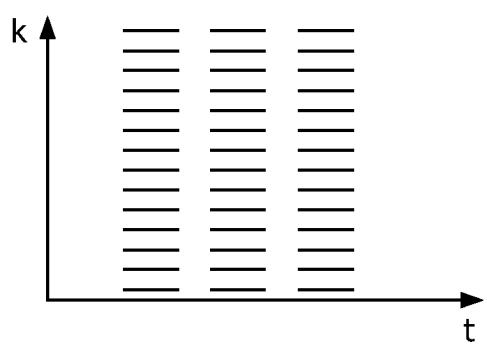
FIG. 3a and FIG. 3b are examples for two different encoding schemes.
Figure 3B:
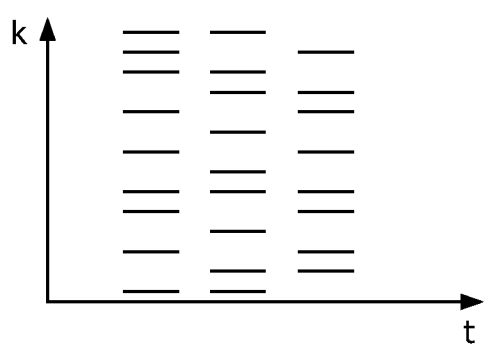

FIG. 3a and FIG. 3b show examples for two different encoding schemes. FIG. 3a shows uniform encoding used in standard MRI for chemical shift encoding, or to capture dynamic processes. In FIG. 3b Sub-sampling is performed in a random fashion for scan acceleration. Missing information is recovered by means of compressed sensing reconstruction.

As an example a 3D time-resolved (6 dynamics) DCE measurement may be performed using three-point Dixon multi-echo encoding. Before contrast media (Gd) application a single conventional (not under-sampled) water/fat resolved 3D scan is performed using the sequence shown in FIG. 2a, giving the initial water/fat distribution and the corresponding $\Delta B_0$ map. After this scan the sequence is switched to an under-sampling mode, means that less profiles are acquired in the chemical shift-encoding and also in the temporal dimension using a sequence as shown in FIG. 2b.

Under-sampling is thus performed in the k-TE-t dimension. Several 3D dynamics are acquired using an appropriate under-sampling factor (e.g. 3-4) during Gd uptake. Data are reconstructed using a DCE water/fat resolved k-t CS reconstruction. In this reconstruction the initially obtained $\Delta B_0$ map (before Gd application) and potentially water and fat distribution could be used as sparsifyers, and included a-priory information.

Speculating that the contrast media does not affect the fat signal, prior information from the initial chemical shift imaging would be sufficient to subtract the fat signal from the DCE data. In this case the DCE measurement could be further accelerated by means of k-t CS. In this water/fat resolved DCE data become available, with better quality and higher temporal resolution.

The invention can be used to facilitate for example accelerated water/fat resolved DCE breast cancer diagnosis. The accelerated water/fat separation algorithm delivers a $\Delta Bo$ map for free. This reflects the main field inhomogeneity ($\Delta Bo$) and is influenced by local tissue susceptibility changes, which could be of additional of diagnostic value, helping to characterize tumor tissue. Separated fat tissue signals could also bear diagnostic information helping to characterize tissue on a structural level. DCE fat data could also contribute to the diagnoses.

The invention claimed is:

1. A method of performing dynamic contrast enhanced magnetic resonance imaging of an object with signal separation for water and fat, the method comprising:
    a magnetic resonance imaging apparatus acquiring magnetic resonance datasets in the k-space using Dixon acquisition in a chemical shift encoding space and dynamic time resolution in a dynamic time space, wherein the dataset acquisition is performed employing undersampling;
    applying a compressed sensing reconstruction technique in the k-space, the chemical shift encoding space and the dynamic time space, said compressed sensing reconstruction resulting in reconstructed datasets; and
    performing Dixon reconstruction on the reconstructed datasets and dynamic contrast analysis on the Dixon reconstructed datasets.

2. The method of claim 1, wherein the datasets are acquired in the k-space, chemical shift encoding space and the dynamic time space employing undersampling.

3. The method of claim 1, wherein the compressed sensing reconstruction and Dixon reconstruction are performed together in a combined optimization process.

4. The method of claim 3, further comprising acquiring an a priori water-fat image on the object, wherein the compressed sensing reconstruction comprises:
    determining an MR signal model of an expected water-fat image, and
    iteratively linearizing the signal model, said iteration being initialized with the a priori water-fat image.

5. The method of claim 4, wherein the a priori water-fat image comprises a water signal, a fat signal and a field map, wherein the compressed sensing reconstruction is performed assuming constraints regarding a temporal behavior of the water signal and/or fat signal and/or field map in the dynamic time space.

6. The method of claim 4, wherein the a priori water-fat image is acquired with full sampling in the k-space and the chemical shift encoding space.

7. The method of claim 1, wherein the k-space centre is fully sampled.

8. The method of claim 1, wherein the undersampling is performed randomly or quasi-randomly.

9. The method of claim 1, wherein the magnetic resonance datasets are acquired employing parallel imaging.

10. The method of claim 1, wherein the Dixon acquisition is a multi-echo Dixon acquisition.

11. The method of claim 1, wherein the Dixon acquisition is a single-point Dixon acquisition.

12. A non-transitory computer program product comprising computer executable instructions to cause a magnetic resonance imaging apparatus to perform the method of claim 1.

13. A magnetic resonance imaging apparatus for performing dynamic contrast enhanced magnetic resonance imaging of an object with signal separation for water and fat, the apparatus comprising:
- a magnetic resonance imaging scanner for acquiring magnetic resonance image data,
- a controller adapted for controlling a scanner operation of acquiring magnetic resonance datasets in the k-space using multi-echo Dixon acquisition in a chemical shift encoding space and dynamic time resolution in a dynamic time space, wherein the controller is further adapted to perform the dataset acquisition employing undersampling,
- a data reconstruction system adapted for applying a compressed sensing reconstruction technique in the k-space, the chemical shift encoding space and the dynamic time space, said compressed sensing reconstruction resulting in reconstructed datasets, wherein the data reconstruction system is further adapted for performing Dixon reconstruction on the reconstructed datasets and dynamic contrast analysis on the Dixon reconstructed datasets.

14. The magnetic resonance imaging apparatus of claim 13, wherein the data reconstruction system is adapted for performing the compressed sensing reconstruction technique and the Dixon reconstruction together in a combined optimization process.

15. The magnetic resonance imaging apparatus of claim 14, wherein the magnetic resonance imaging apparatus is configured to acquire an a priori water-fat image on the object, and wherein the data reconstruction system is adapted for performing the compressed sensing reconstruction by:
- determining an MR signal model of an expected water-fat image, and
- iteratively linearizing the signal model, said iteration being initialized with the a priori water-fat image.

16. The magnetic resonance imaging apparatus of claim 15, wherein the a priori water-fat image comprises a water signal, a fat signal and a field map, and wherein the data reconstruction system is adapted for performing the compressed sensing reconstruction assuming constraints regarding a temporal behavior of the water signal and/or fat signal and/or field map in the dynamic time space.

17. The magnetic resonance imaging apparatus of claim 15, wherein the magnetic resonance imaging apparatus is configured to acquire the a priori water-fat image with full sampling in the k-space and the chemical shift encoding space.

18. The magnetic resonance imaging apparatus of claim 13, wherein the magnetic resonance imaging apparatus is configured such that the k-space centre is fully sampled.

19. The magnetic resonance imaging apparatus of claim 13, wherein the magnetic resonance imaging apparatus is configured such that the undersampling is performed randomly or quasi-randomly.

20. The magnetic resonance imaging apparatus of claim 13, wherein the magnetic resonance imaging apparatus is configured such that the magnetic resonance datasets are acquired employing parallel imaging.

* * * * *